US011216442B2

(12) United States Patent
Teer et al.

(10) Patent No.: US 11,216,442 B2
(45) Date of Patent: Jan. 4, 2022

(54) LARGE DATA SET NEGATIVE INFORMATION STORAGE MODEL

(71) Applicant: H. LEE MOFFITT CANCER CENTER & RESEARCH INSTITUTE, INC., Tampa, FL (US)

(72) Inventors: Jamie K. Teer, Odessa, FL (US); Ruizheng Liu, Tampa, FL (US); Guillermo Gonzalez-Calderon, Tampa, FL (US); Rodrigo Carvajal-Pelaez, Tampa, FL (US)

(73) Assignee: H. LEE MOFFITT CANCER CENTER AND RESEARCH INSTITUTE, INC, Tampa, FL (US)

( * ) Notice: Subject to any disclaimer, the term of this patent is extended or adjusted under 35 U.S.C. 154(b) by 116 days.

(21) Appl. No.: 15/751,955

(22) PCT Filed: Aug. 12, 2016

(86) PCT No.: PCT/IB2016/054868
§ 371 (c)(1),
(2) Date: Feb. 12, 2018

(87) PCT Pub. No.: WO2017/025935
PCT Pub. Date: Feb. 16, 2017

(65) Prior Publication Data
US 2018/0239797 A1 Aug. 23, 2018

Related U.S. Application Data

(60) Provisional application No. 62/204,526, filed on Aug. 13, 2015.

(51) Int. Cl.
G06F 16/215 (2019.01)
G06F 16/23 (2019.01)
(Continued)

(52) U.S. Cl.
CPC ........ *G06F 16/2365* (2019.01); *G06F 16/215* (2019.01); *G06F 16/22* (2019.01);
(Continued)

(58) Field of Classification Search
CPC .. G06F 17/18; G06F 16/2228; G06F 16/2365; G06F 16/215; G06F 16/335; G16B 30/00; G16B 30/10
See application file for complete search history.

(56) References Cited

U.S. PATENT DOCUMENTS 5,966,712 A 10/1999 Sabatini et al.
2001/0053957 A1 12/2001 Blair et al.
(Continued)

Primary Examiner — Marcin R Filipczyk
(74) Attorney, Agent, or Firm — Meunier Carlin & Curfman LLC

(57) ABSTRACT

Systems and methods for storing large data sets, such as genetic sequence information. Within a "targeted subset" of positions with information, the system stores, both variant states and missing states at each position. Reference states are not stored, but are inferred within the targeted subset when neither a variant nor a missing state is stored at a given position. The absence of a variant state at a given position is assumed to be a reference state. The criteria for missing data are defined in pre-processing and are customizable based on the use case. For example, each data point may represent the genetic information of a sample at a position in the genome. The targeted subset may represent those positions that were included in a sequencing test.

15 Claims, 8 Drawing Sheets

(51) Int. Cl.
  *G06F 16/22*   (2019.01)
  *G16B 50/00*   (2019.01)
  *G16B 30/00*   (2019.01)
  *G16B 50/50*   (2019.01)
  *G16B 30/10*   (2019.01)

(52) U.S. Cl.
  CPC ............. *G16B 30/00* (2019.02); *G16B 30/10* (2019.02); *G16B 50/00* (2019.02); *G16B 50/50* (2019.02)

(56) References Cited

U.S. PATENT DOCUMENTS

2005/0272070 A1* 12/2005 Ehrich ................ C12Q 1/6858
                                                    435/6.12
2008/0077607 A1   3/2008 Gatawood et al.
2012/0310980 A1  12/2012 Dodd et al.
2013/0191351 A1   7/2013 Baym et al.
2016/0306923 A1* 10/2016 van Rooyen .......... G06N 3/002

* cited by examiner

Negative Storage Model

☐ = subset (compact)
▨ = stored reference
■ = stored missing
░ = not stored
▩ = stored variant

FIG. 3

LARGE DATA SET NEGATIVE INFORMATION STORAGE MODEL

BACKGROUND

Genomic information is an important molecular marker for human diseases, including acquired diseases such as cancer and both rare and common inherited diseases such as Cystic Fibrosis and hypertension. Current data storage strategies associated with genomic information focus on storing all known information. These strategies may result in a need to store up to 3-6 billion pieces of information per individual. FIG. 1 illustrates a small-scale example in which there are 77 elements stored, however, this would be much larger in a real-world example. In particular, for each position, either a reference value, a variant value, or a missing value is stored. As shown, no information is "not stored." With regard to genomic information and other large data sets, the vastness of the storage need creates a burden for physical storage as well as computational resources to access the data.

A "reference value" in the above example is a nucleotide at a given position in the Human Genome Reference Sequence. As is understood, sequence data is often compared to a reference genome, e.g., like puzzle pieces to the picture on the box. Reference values can be stored in the same database, in linking databases, or in another location. A unique key may be used to link the reference values to the experimental positions. For example, in genetic sequence data, a unique key can be constructed from the chromosome, position, and reference version. To uniquely identify a variant, the model can use chromosome, positions, reference base, and variant base. A "variant" is any value that is different from the reference at a given position.

An alternative to storing all known information is shown in FIG. 2, which illustrates a strategy to store only variants or differences from a known reference value. In FIG. 2, there are only 10 elements to store; however, as shown, the strategy fails to account for positions that are missing. In particular, the "not stored" positions are wrongly assumed to be reference values. This results in a severe loss of precision, especially when different, non-overlapping genomic tests have been performed. This also results in increasing the risk of false negatives when different subsets are tested.

SUMMARY

The present disclosure describes systems and methods for storing large data sets by reducing storage by storing what is NOT known. The method defines a "positive region" (a universe of possibilities where we can generally assume to have knowledge) for each sample. These regions may differ between samples to account for different tests. Then, the important genetic variants for each sample are stored using a unique key. Finally, areas of missing data (absent or low quality) are also stored. To determine what the precise status of a sample is at a given difference position, we first ask whether a position lies within a positive region. If so, the position is queried for either a difference or for missing data. If neither are found, the status is "reference" or no change. If missing data is found, the sample is excluded from further calculations or reporting at that position. Assuming missing data rates of 5-15%, this results in a savings of 85-95% per sample, allowing smaller physical storage and computational resource requirements. Missing data may be stored as "regions" as opposed to individual positions, further reducing storage requirements. Additionally, a negative storage model incentivizes the collection of high quality data up front by upending the storage requirements at the end (more resources required for "less" data, as we store what's missing).

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views:

FIG. 3 illustrates an example storage model where negative information is stored;

DETAILED DESCRIPTION

Figure 1:
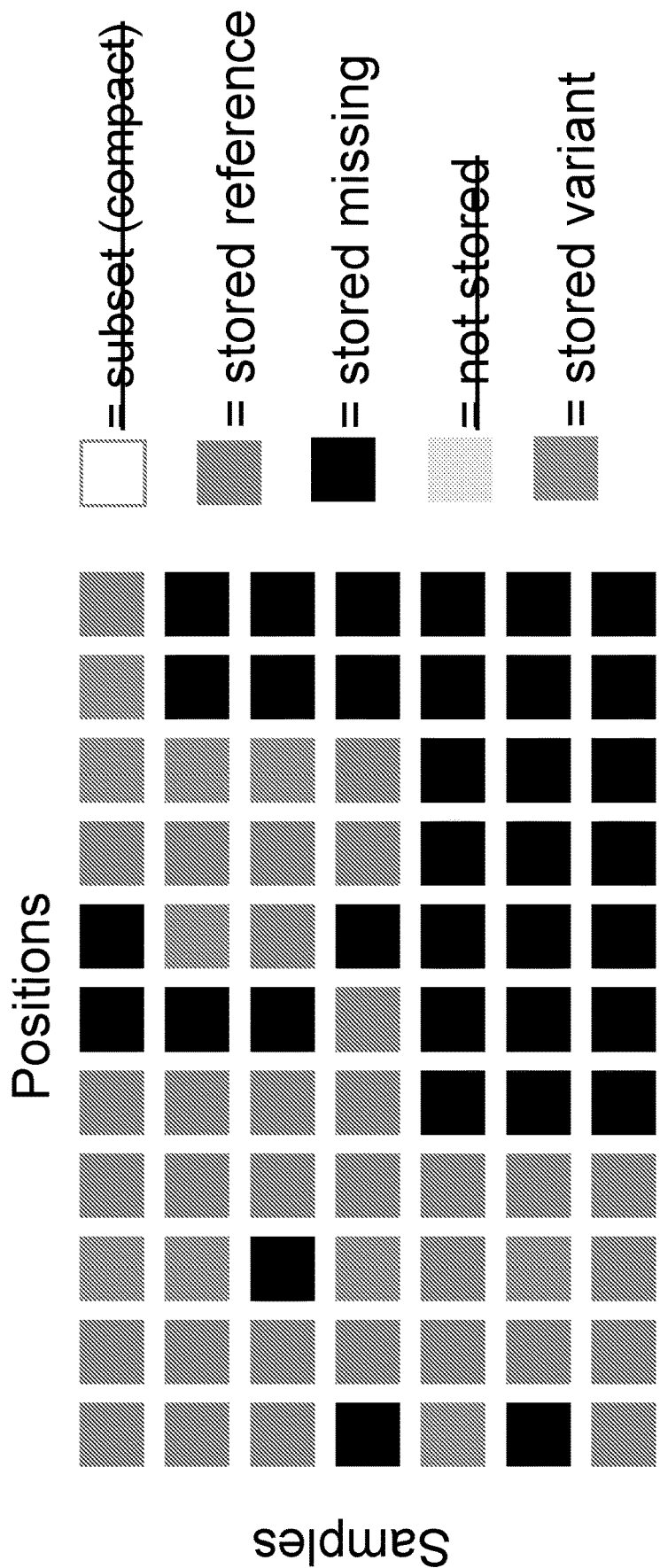
FIG. 1 illustrates an exemplary storage model where all data is stored.

The present disclosure describes system and methods for storing large data sets, such as genetic sequence information. Within a "targeted subset" of positions with information, the system of the present disclosure stores, both variant states and missing states at each position. Reference states are not stored, but are inferred within the targeted subset when neither a variant nor a missing state is stored at a given position. The above is in contrast to conventional systems where only variants or differences are stored, and the absence of a variant state at a given position is assumed to be a reference state.

In accordance with the present disclosure, criteria for missing data are defined in pre-processing and are customizable based on the use case. For example, each data point may represent the genetic information of a sample at a position in the genome. The targeted subset may represent those positions that were included in a sequencing test.

Queries may be run against the target subset as follows:

IF a queried position is NOT in subset, the system returns a status of "unknown/missing";

IF a queried position is in subset AND no data stored for position, the system returns a status that is inferred to be "reference/non-variant";

IF a queried position is in subset AND variant stored for position, the system returns a status of "variant"; and IF a queried position in is subset AND "unknown/missing" is stored for the queried position, the system returns a status of "unknown/missing."

With reference to FIG. 3, there is illustrated an implementation of a storage model in accordance with the present disclosure. As illustrated, subsets are identified. For example, three different subsets across 7 individuals (rows) may be defined among the example 77 positions of FIG. 3. Other numbers of subsets may be defined in accordance with the sampled data. Within each subset, for each position, data is stored if the value is a "variant" or data is "missing." If data is not stored, it is assumed to be a predetermined reference value.

For positions outside of the identified subsets, no data is stored, as these positions do not form a part of the sampled data (e.g., genetic information). Thus, the positions outside of the identified subsets formed no part of the stored information. As a result, the implementation of the storage model of the present disclosure stores 18 elements among the 77 total possible positions while providing a higher level of precision than is possible using the storage model of FIG. 2 and reducing the storage requirement from 77 to 18 elements with respect to the storage model of FIG. 1.

In a variation of the storage model of FIG. 3, the data may be stored as regions, whereby a start and end point is identified. For example, contiguous data of like kind may be identified as a region. Thus, the two "stored missing" values in the uppermost subset may be stored as a single region. As such, this variation reduces the storage requirement from 18 elements to 17 elements. Although not shown, other contiguous data of like kind was stored in the storage model of FIG. 3, such data may also be represented by a region.

Figure 2:
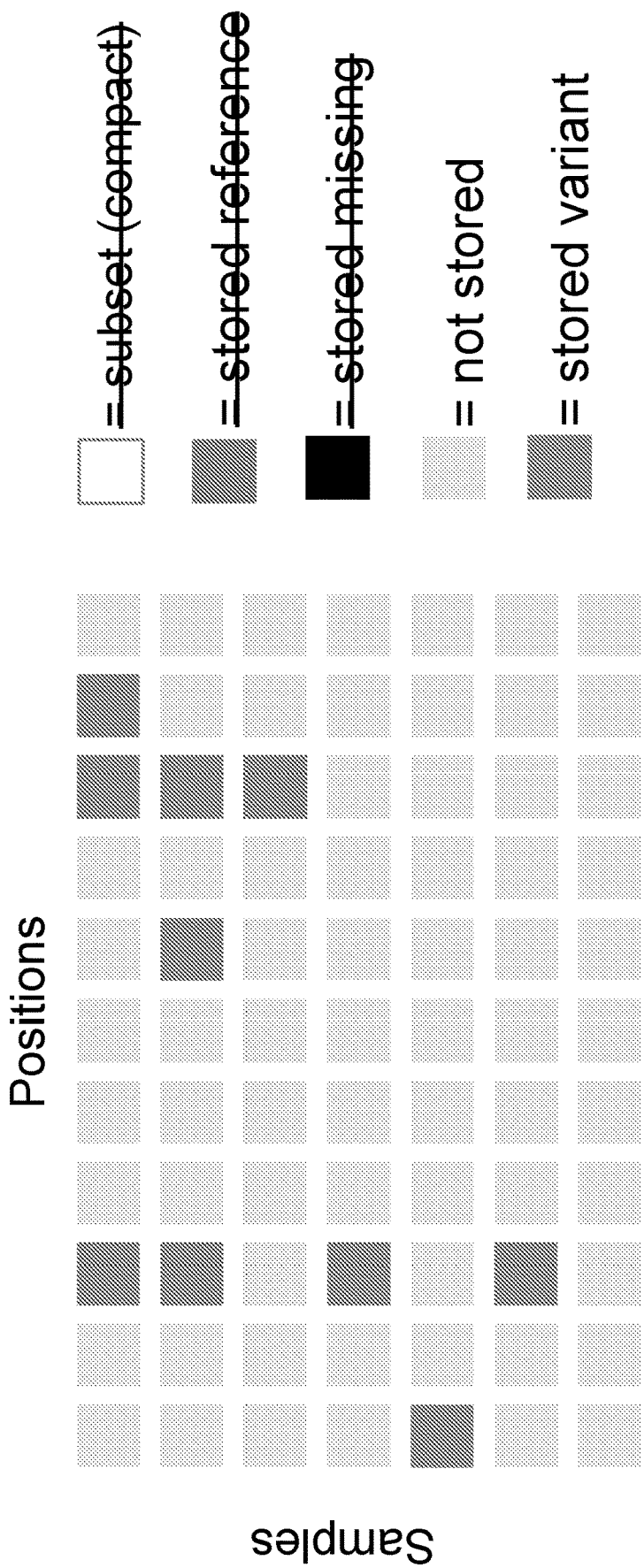
FIG. 2 illustrates an example storage model where only variants are stored.
Figure 4A:
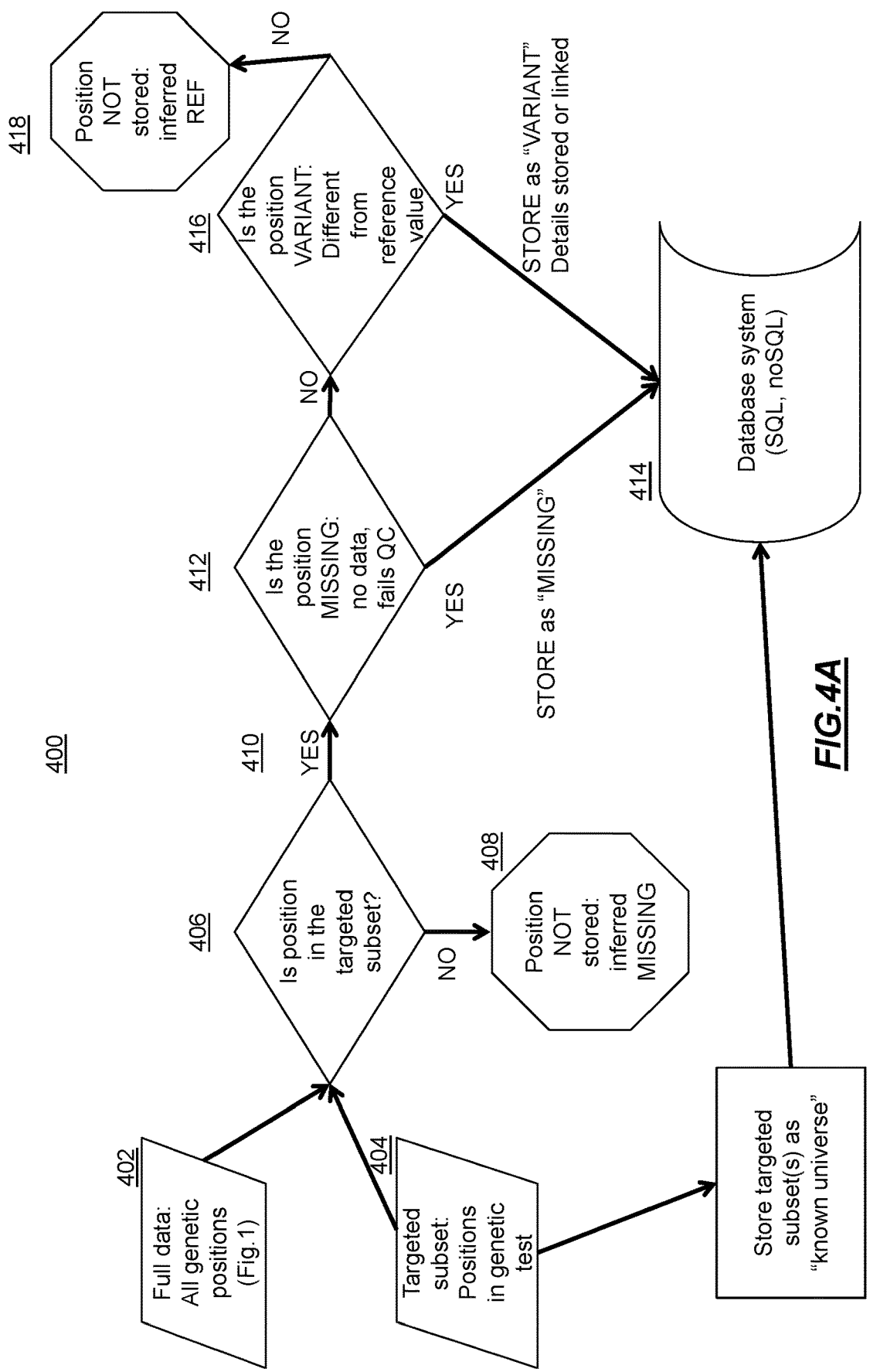
FIGS. 4A and 4B illustrate example operational flows to encode or compress information in the storage model of FIG. 3.

In addition or alternatively to storing elements as regions, bit arrays (integer representations of large sets of binary values) can be used to store information, including but not limited to target subset definitions (which are often applicable to many samples) and missing data definitions (which can be both contiguous and sparse). Bit arrays enable more compact storage of positive data, and enable highly efficient querying via binary math Encoding or Compressing Data into the Negative Storage Model FIG. 4A illustrates an operational flow 400 to encode/compress full data 402 (as represented by FIG. 1) into the storage model of FIG. 3. While the operational flow 400 describes a process with particular reference to genomic information, it is contemplated by the present disclosure that other types of data may be stored in the storage model of FIG. 3. Examples of such other data are discussed below. At 404, a targeted subset of known information is defined. For example, the targeted subset may include genomic positions targeted by a clinical genetic test or targeted sequencing experiment, items that are the subject of a survey, or others. The number of targeted subsets is usually smaller than the number of samples/subjects, as many subjects will have the same test/survey. The targeted subsets limit the positions to those in the "universe of possibilities" and are stored in the database system 414 for later use in decoding.

At 406 it is determined for every position or element in the full data 402 whether the position is in the targeted subset 404. If no, position is not stored, but inferred to be missing at 408. If yes, then at 410, positions are then examined for missing state at 412. The definition of "missing" may vary based on end-user needs and is further described below with reference to FIG. 4B. Missing positions are then stored in database 414. Non-missing positions are tested at 416 to determine if the value is the same as or different from a reference value. Variations from the reference are stored in database 414. Additional information related to the variant state (e.g., the actual value and other related values) are also stored in database 414, or may be linked from another database system. At 418, positions that are the reference value are not stored (discarded), but will be inferred during decoding.

Figure 4B:
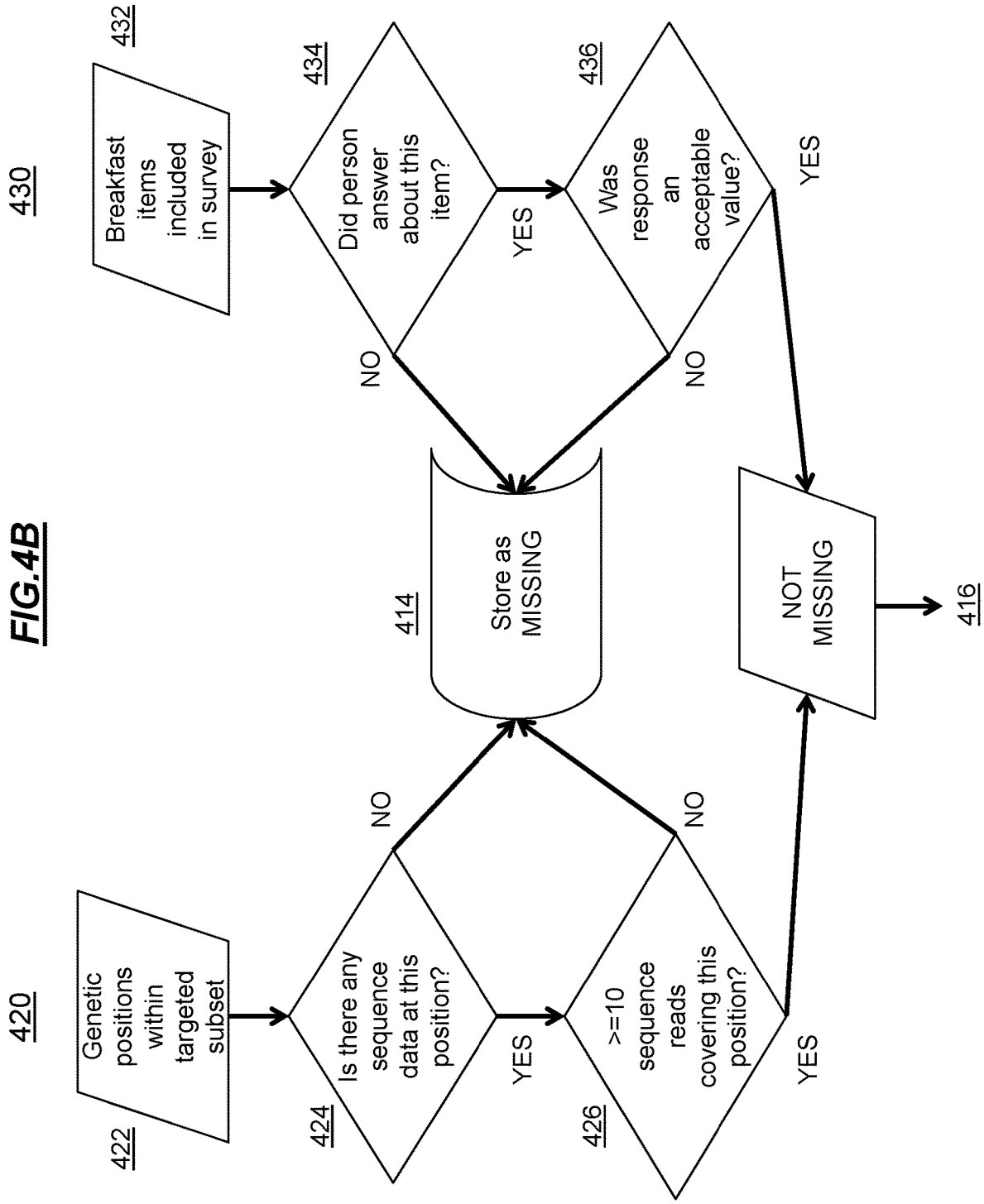

FIG. 4B illustrates an example operational flow to determine missing data. Missing data can be defined in many ways, but is generally defined to be those positions at which there is no information. Missing positions can include positions that were in a targeted subset, but did not have any data (e.g., a failed position in a genetic test, unanswered question in a survey), positions where the data quality was insufficient for distinguishing reference from variant values based on user criteria, or even positions that may have sufficient data, but for other reasons are desired to be masked.

The operational flow of FIG. 4B may be performed on data 410 input to the operation flow 400 that has passed the targeted subset decision 406 of FIG. 4A (data 422 in FIG. 4B). A genetic sequence example 420 is shown, where a position is first assessed for any data at 424, and then assessed for data of a specific quality at 426. Positions without data, or with data of insufficient quality are stored in database 414, while positions with data of sufficient quality are passed after 426 to process 416 for evaluation of variance. In a survey example 430, input data is different breakfast items asked about in a questionnaire. For each item, at 432, it is first determined whether an individual answered the question at 434. Positions without data, or with data of insufficient quality are stored in database 414. If an answer is given, it is determined at 436 whether the answer was allowable (e.g., "blue" is not an allowable answer for a yes/no question, resulting in a missing value to be stored). The positions with data of sufficient quality are passed at 436 to process 416 for evaluation of variance.

Thus, from the examples 420 and 430, the definition of the "missing" state is flexible and can either be defined by a distributor, or made customizable by users. The flexibility enables the establishment of different quality tiers by storing a value with the 'missing' state. For example, genetic sequence data may have more strict requirements for clinical use compared to research use. Therefore, during the test for missing (412), two separate processes may be run, e.g., one very strict for clinical use, one more lenient for research use. Positions determined to be missing would include a value indicated the process that determined the missing state (e.g., 'clinical', 'research', or both). Any number of different missing tiers can be defined by values stored with, or linked to the missing state.

Figure 5:
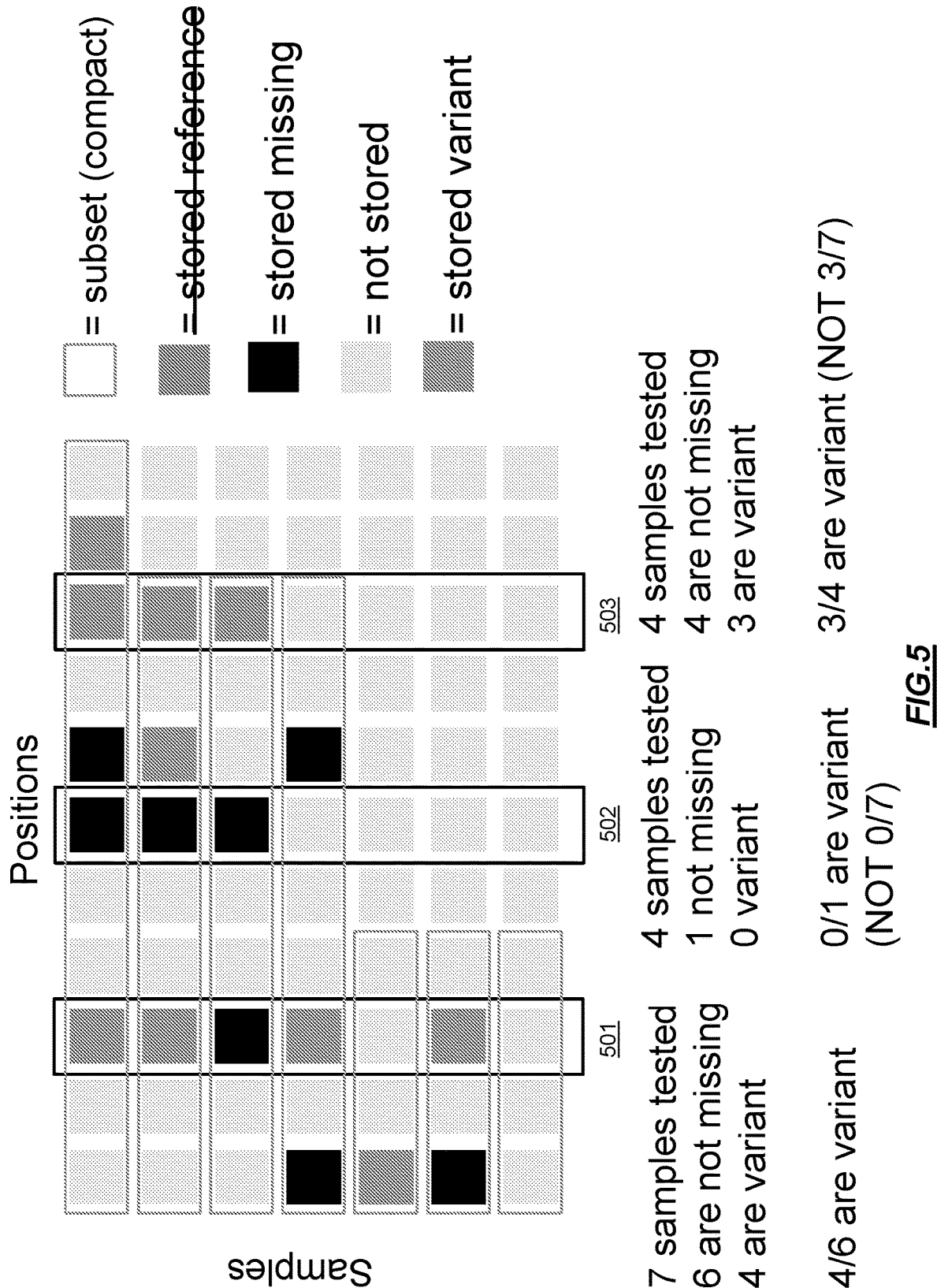
FIG. 5 illustrates querying the storage model of FIG. 3.

FIG. 5 illustrates querying the storage model of FIG. 3. As shown, queries may be run against positions (e.g., 501, 502 and 503) for each sample. For a query of position 501, seven samples are part of the "known universe" (i.e., the defined subsets include all seven samples of the data set). Here it can be determined that six are not missing and 4 out of 6 contain variant values. Comparing this result with the same query run on the storage model of FIG. 2, the result would be different as FIG. 2 would inaccurately return a result of 4 out of 7 having variant values. For a query of position 502, four samples are part of the "known universe" (i.e., the defined subsets include for samples of the data set). Here it can be determined that one is not missing and 0 out of 1 have variant values. Comparing this result with the same query run on the storage model of FIG. 2, the incorrect result would be 0 out of 7 having variant values. For a query of position 503, four samples are part of the "known universe" (i.e., the defined subsets include four samples of the data set). Here it can be determined that four are not missing and 3 out of 4 have variant values. Comparing this result with the same query run on the storage model of FIG. 2, the incorrect result would be 3 out of 7 having variant values.

Thus, as would be understood, the storage model of the present disclosure provides for high accuracy while reducing storage requirements for large data sets of information.

Decoding or Decompressing Data from the Negative Storage Model

Figure 6:
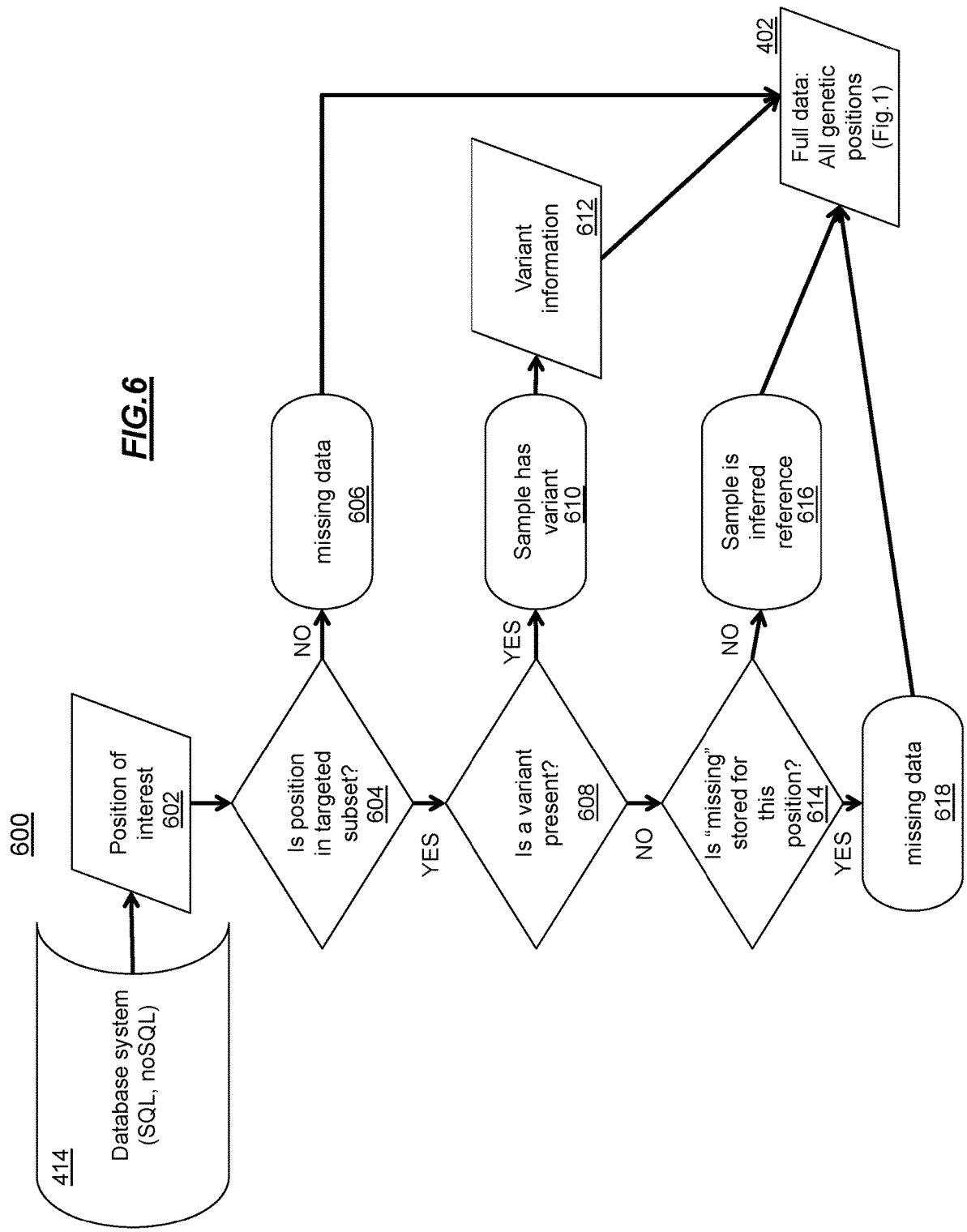
FIG. 6 illustrates an example operational flow to decode or decompress information in the storage model shown in FIG. 5.

FIG. 6 illustrates an example operational flow 600 to query and decode/decompress information in the storage model shown in FIG. 3. At 602, a position of interest to be queried from the storage model as stored in database 414 is identified. At 604, it is determined if the position is in the subset(s) associated with entries in the storage model. If no, then at 606, the user is notified that there is no data for the requested position of interest for a given sample or individual, or the position is ignored for further summarization or querying. If yes, then at 604, the position is in a subset(s) associated with the storage model, and therefore is within the universe of possible knowledge.

Next, at 608, it is determined if a variant is present. If so, then at 610 the method returns an indication that the sample has a variant. Further information associated with the variant position can be returned at 612. If not, then at 614, it is determined if the position is "stored missing." If not, then at 616, it is reported that the sample at the position of interest has a reference value. If so at 614, then at 618, it is reported that there is missing data for the position of interest, and it is then ignored.

Thus, in accordance with the operational flow 600, the returned states at each position (variant, reference, or missing) are used to reconstitute the original full data 402, thus preserving the original data with greatly reduced storage requirements.

While all the above examples of storing and querying data have been demonstrated respect to genomic information, the storage models of the present disclosure may be used for other types of large data sets. Other uses include, but are not limited to, healthcare where clinical pathways (describing a decision tree for "default" procedures to be performed on a patient). The target/realm of possibilities may be those actions/decisions appropriate for a disease. A non-standard outcome/result of a given procedure may be stored as a "variant." Pathway procedures that have not been performed may be "stored missing" and may be deleted as completed according to the pathway. Similarly, in healthcare, the storage model may be used as in a patient encounter database. The target/realm of possibilities may be procedures, forms, questions (i.e., everything that needs to happen with a patient). The outcome/result of a given procedure, or status of a form or questionnaire may be stored as a "variant." Procedures/forms that have not been performed/returned may be stored as "missing data."

In other possibilities, the storage model may be used for healthcare or other survey research as part of storing completion of different surveys. The target/realm of possibilities may include those surveys a person is eligible to complete, which are stored as "variants." Surveys not completed for further follow-up may be stored as "missing data." Upon completion, the "missing data" may be deleted (assume no data means completed survey).

In yet other possibilities, the storage model be used in market research, where opinions of people in relation to businesses are stored. The target/realm of possibilities may include a list of businesses within certain distance or that are "liked" in a social network. The opinion on visited businesses may be stored as "variants." Information on businesses not visited or "like" links not clicked may be stored as "missing data." Assume that other businesses were visited, links were clicked, but no opinion was provided (this could also be inverted to assume businesses that are NOT visited, and store those that are visited).

Data on polls/questionnaires can also be stored with this model. The reference value for a given question can be the most popular response, which is then inferred. The targeted subset includes the questions a given respondent was asked (based on the version of the poll/questionnaire). Reference values (the popular answer) would not be stored, but inferred upon decoding. Unanswered questions, responses of "I don't know", "Not applicable", etc. would be stored as missing, while the less frequent responses would be stored as variant. Coding and decoding would proceed as in FIGS. 4A, 4B and 6.

Preliminary Performance Results

The negative storage model of the present disclosure has been implemented using a publically available genetic sequence dataset (The Cancer Genome Atlas: TCGA). Somatic mutation data covering ~40 million positions was encoded across 367 samples in the described Negative Storage Model. The data was loaded to a full storage model (as in FIG. 1). Queries were submitted to both systems, and identical results were returned, demonstrating the ability of the Negative Storage Model to reconstitute the full data.

Compared to the full storage model, the number of rows stored in the database for the Negative Storage model was 0.9% (i.e., a savings of >99%). Loading the data to the Negative Storage model took between 0.1%-1% of the length of time compared to the full storage model based on the database system used. Querying time was generally faster for the Negative Storage model, with query times ranging from 100% (the same) to 1% of that needed by the Negative Storage model. The actual disk space taken by the Negative Storage model ranged from 2.5%-1% of that taken by the full storage model. Although these results are not meant to warrant or guarantee any specific level of performance, they demonstrate the Negative Storage Model is 1) effective, 2) able to be reduced to practice, and 3) a significant improvement over existing practice.

Cost Advantages

Common practice is to store what is known. Therefore, the more known information, the higher the storage costs. The Negative Storage Model includes storing what is NOT known. In encoding, known information (reference) is not actually stored, but inferred during decoding. Therefore, this storage model may result in lower storage costs when more information is known: newly known reference values would be inferred, and not stored as "missing" values.

Figure 7:
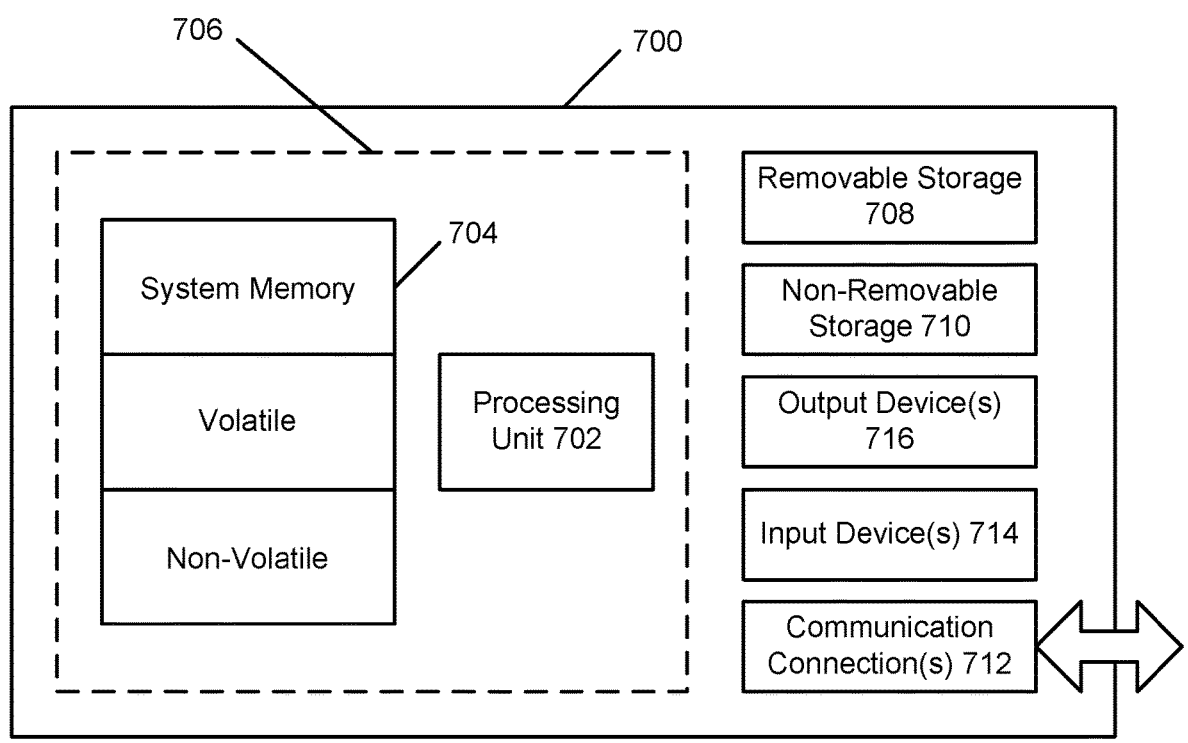
FIG. 7 shows an example computing environment data query.

FIG. 7 shows an exemplary computing environment in which example implementations and aspects may be implemented. The computing system environment is only one example of a suitable computing environment and is not intended to suggest any limitation as to the scope of use or functionality.

Numerous other general purpose or special purpose computing system environments or configurations may be used. Examples of well-known computing systems, environments, and/or configurations that may be suitable for use include, but are not limited to, personal computers (PCs), server computers, handheld or laptop devices, multiprocessor systems, microprocessor-based systems, network PCs, minicomputers, mainframe computers, embedded systems, distributed computing environments that include any of the above systems or devices, and the like.

Computer-executable instructions, such as program modules, being executed by a computer may be used. Generally, program modules include routines, programs, objects, components, data structures, etc. that performs particular tasks or implement particular abstract data types. Distributed computing environments may be used where tasks are performed by remote processing devices that are linked through a communications network or other data transmission medium. In a distributed computing environment, program modules and other data may be located in both local and remote computer storage media including memory storage devices.

An exemplary system for implementing aspects described herein includes a computing device, such as computing device 700. In its most basic configuration, computing device 700 typically includes at least one processing unit 702 and memory 704. Depending on the exact configuration and type of computing device, memory 704 may be volatile (such as random access memory (RAM)), non-volatile (such as read-only memory (ROM), flash memory, etc.), or some combination of the two. This most basic configuration is illustrated in FIG. 3 by dashed line 706.

Computing device 700 may have additional features/functionality. For example, computing device 700 may include additional storage (removable and/or non-removable) including, but not limited to, magnetic or optical disks or tape. Such additional storage is illustrated in FIG. 3 by removable storage 708 and non-removable storage 710.

Computing device 700 typically includes a variety of computer readable media. Computer readable media can be any available media that can be accessed by device 700 and include both volatile and non-volatile media, and removable and non-removable media.

Computer storage media include volatile and non-volatile, and removable and non-removable media implemented in any method or technology for storage of information such as computer readable instructions, data structures, program modules or other data. Memory 704, removable storage 708, and non-removable storage 710 are all examples of computer storage media. Although not shown, the computer storage may include network attached storage where another computer system acts as a storage device for the computer system 700. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 700. Any such computer storage media may be part of computing device 700.

Computing device 700 may contain communications connection(s) 712 that allow the device to communicate with other devices. Computing device 700 may also have input device(s) 714 such as a keyboard, mouse, pen, voice input device, touch input device, etc. Output device(s) 716 such as a display, speakers, printer, etc. may also be included. All these devices are well known in the art and need not be discussed at length here.

It should be understood that the various techniques described herein may be implemented in connection with hardware or software or, where appropriate, with a combination of both. Thus, the processes and apparatus of the presently disclosed subject matter, or certain aspects or portions thereof, may take the form of program code (i.e., instructions) embodied in tangible media, such as floppy diskettes, CD-ROMs, hard drives, or any other machine-readable storage medium where, when the program code is loaded into and executed by a machine, such as a computer, the machine becomes an apparatus for practicing the presently disclosed subject matter.

Although exemplary implementations may refer to utilizing aspects of the presently disclosed subject matter in the context of one or more stand-alone computer systems, the subject matter is not so limited, but rather may be implemented in connection with any computing environment, such as a network or distributed computing environment. Still further, aspects of the presently disclosed subject matter may be implemented in or across a plurality of processing chips or devices, and storage may similarly be affected across a plurality of devices. Such devices might include PCs, network servers, and handheld devices, for example.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A method for encoding and storing large datasets into a negative storage model for storage in a database, comprising:
    defining a missing state as at least one of a position containing no data or a position having data that fails to meet a predetermined sufficient quality such that the data cannot be distinguished from a reference value;
    identifying a targeted subset of the dataset that has known information,
    determining, for every position in the dataset, whether a particular position is in the targeted subset, and
    for only positions within the targeted subset and for each data point,
        determining positions within the target subset that contain no data and positions within the target subset that fail to meet the predetermined quality to identify missing states;
    storing the missing states in the database for each identified data point; and
    identifying variations from the reference value;
        when a variation from the reference value is identified, storing the variation for each identified data point in the database; and
        when a variation from the reference value is not found, discarding each identified data point,
    wherein only data points that are (1) not the reference value or missing and (2) within the targeted subset are stored in the database.

2. The method of claim 1, further comprising discarding the positions not in the targeted subset and not storing them in the database.

3. The method of claim 1, further comprising comparing only non-missing positions to the reference value.

4. The method of claim 3, further comprising storing additional information related to the variation in the database.

5. The method of claim 4, wherein the additional information comprises the actual value of the variation.

6. The method of claim 1, further comprising determining missing states further comprising defining missing states to be data points in the targeted subset that did not have any data, data points where a data quality was insufficient to distinguish the variation, data points that are masked, or data points that contain unallowable information.

7. The method of claim 6, wherein missing values are user defined for a particular targeted subset of the dataset to be stored in the database.

8. The method of claim 6, further comprising determining plural missing states.

9. The method of claim 8, wherein the identifying missing states for each data point comprises:
   determining the plural missing states for each data point; and
   storing, in accordance with the determining, the plural missing states for each identified data point in the database.

10. The method of claim 1, wherein the targeted subset of the dataset is genomic positions.

11. A database storage apparatus for storing a compressed negative storage model, comprising:
   a processor;
   a memory that contains computer executable instructions that when executed by the processor causes the database storage apparatus to:
   defining a missing state as at least one of a position containing no data or a position having data that fails to meet a predetermined sufficient quality such that the data cannot be distinguished from a reference value;
   identify targeted subset of the dataset that has known information,
   determining, for every position in the dataset, whether a particular position is in the targeted subset, and
   for only positions within the targeted subset and for each data point,
      determining positions within the target subset that contain no data and positions within the target subset that fail to meet the predetermined quality to identify missing states;
   store the missing states in the database for each identified data point; and
   identify variations from the reference value;
      when a variation from the reference value is identified, storing the variation for each identified data point in the database; and
      when a variation from the reference value is not found, discarding each identified data point,
   wherein only data points that are (1) not the reference value or missing and (2) within the targeted subset are stored in the database.

12. The database storage apparatus of claim 11, further comprising instructions to discard the positions not in the targeted subset and not storing them in the database.

13. The database storage apparatus of claim 11, further comprising instructions to compare only non-missing positions to the reference value.

14. The database storage apparatus of claim 11, further comprising instructions to define missing states to be data points in the targeted subset that did not have any data, data points where a data quality was insufficient to distinguish the variation, data points that are masked, or data points that contain unallowable information.

15. The database storage apparatus of claim 11, further comprising instructions to determine plural missing states; and store, in accordance with the determining, the plural missing states for each data point in the database.

* * * * *